United States Patent
Hayashi et al.

[11] Patent Number: 6,045,524
[45] Date of Patent: Apr. 4, 2000

[54] JOINT OF ORTHOTIC APPARATUS

[75] Inventors: Masayasu Hayashi; Tetsuro Suganuma, both of Nagoya, Japan

[73] Assignees: Kabushiki Kaisha Tatematsu Seisakusho; Takahiro Kogyo Kabushiki Kaisha, both of Aichi-Ken, Japan

[21] Appl. No.: 09/156,921

[22] Filed: Sep. 18, 1998

[30] Foreign Application Priority Data

Dec. 19, 1997 [JP] Japan ..................................... 9-364990
Feb. 13, 1998 [JP] Japan ..................................... 10-048624

[51] Int. Cl.$^7$ ................................. A61F 5/00; A61F 3/00
[52] U.S. Cl. .................................. 602/23; 602/5; 602/16; 601/34; 623/31; 623/26; 482/51
[58] Field of Search ........................ 623/31, 26; 602/16, 602/23, 24, 26, 27, 5; 482/51; 607/48, 49; 601/5, 33–35

[56] References Cited

U.S. PATENT DOCUMENTS

| | | | |
|---|---|---|---|
| 3,358,678 | 12/1967 | Kultsar | 623/26 |
| 3,449,769 | 6/1969 | Mizen | 623/26 |
| 3,535,711 | 10/1970 | Fick | 623/24 |
| 3,732,861 | 5/1973 | Leaneis . | |
| 4,557,257 | 12/1985 | Fernandez | 602/5 |
| 4,697,808 | 10/1987 | Larson . | |
| 4,964,628 | 10/1990 | Poplawski . | |
| 4,969,452 | 11/1990 | Petrofsky | 623/31 |
| 5,060,640 | 10/1991 | Rassmusson | 602/16 |
| 5,112,296 | 5/1992 | Beard | 602/28 |
| 5,282,460 | 2/1994 | Boldt | 623/26 X |
| 5,658,242 | 8/1997 | McKay | 602/16 |

FOREIGN PATENT DOCUMENTS

6-114089 6/1994 Japan .

*Primary Examiner*—Richard J. Apley
*Assistant Examiner*—William LaMarca
*Attorney, Agent, or Firm*—Rosenthal & Osha L.L.P.

[57] ABSTRACT

A joint for an orthotic apparatus is disclosed. The joint includes a main block having arc-shaped grooves formed on opposite sides and a pair of rails separated by each arc-shaped groove. The joint also includes a pair of carriers slidably mounted on the opposite sides of the main block, each carrier having a main rollers in rolling engagement with the arc-shaped groove and a plurality of side rollers adapted to roll on the rails. Attached to each carrier is an arc-shaped rack arranged concentrically with the arc-shaped groove and a base plate for connecting to a long leg supporting member. The joint further includes a pinion gear installed on a bottom part of the main block and in meshing engagement with each arc-shaped rack, and an electric motor for operating the pinion gear.

5 Claims, 7 Drawing Sheets

Fig7

JOINT OF ORTHOTIC APPARATUS

FIELD OF THE INVENTION

This invention pertains to a joint of an orthotic apparatus for use in assisting the walking of paraplegic patients and, in particular, to an electrical orthotic apparatus whose long leg supporting members are operated by an electric motor. Additionally, this invention pertains to an orthotic joint apparatus that makes the coupling and removal of the long leg supporting members to the joint apparatus easier through an attachment.

DESCRIPTION OF THE RELATED ART

In the past, inferior limb braces for paraplegic patients, as described in KOKAI (1994)-0114089, have shown as their basis a pelvic body trunk support part that fits around the pelvis of the wearer. Extending from the pelvic body trunk support part are pillar shaped long leg supporting members that support both the left and right limbs. In this configuration, the braces try to make the walking movement of the wearer smoother by aligning the rotation center of a rocking motion of the long leg supporting members to coincide with the hip joint rotating center of the wearer.

The above-mentioned orthotic devices of the past have been, in general, over-sized as a device. Also, when one wanted to sit down on a wheel chair, the above-mentioned pelvic body trunk support member interfered and did not allow a smooth sitting position. Furthermore, these devices did not have a power-assist apparatus and, therefore, had to be moved by the wearer's own power. Additionally, connecting or removing the left or right long leg supporting member from the joint apparatus required the assistance of other persons.

SUMMARY OF THE INVENTION

In one embodiment of this invention, a long leg supporting member connected to a joint apparatus is operated by a power-assisted apparatus comprising an electric motor to make the movement of the left and right long leg supporting members. In another embodiment, the joint is made so that attachment or removal can be freely done between the joint apparatus and the long leg supporting members through an attachment. The attachment is configured so that a wearer in the seated position on a chair, etc., can attach or remove the joint apparatus to or from the long leg supporting members by himself.

In a first embodiment of the invention, the joint of an orthotic apparatus includes a main block having two sides with an arc-shaped groove on each side and a rail formed concentric with each arc-shaped groove; and a carrier slidably mounted on each side of the main block, each carrier having a main roller in rolling engagement with the arc-shaped groove to allow for a relative rocking movement against the main block and to primarily receive vertically-directed loads. Side rollers are mounted on each carrier and rotate on the rails of the block to receive primarily horizontal loads, wherein multiple side rollers are installed around the main roller. Attached to each carrier is an arc-shape rack arranged concentrically with the arc-shaped groove of the main block and positioned below the side rollers. A base plate is connected to the carrier as a part of the carrier adapted to be connected to a long leg supporting member. The orthotic joint further includes a pinion gear installed on a lower part of the main block and in meshing engagement with the arc-shaped rack of each carrier and an electric motor for driving the pinion gear.

The above mentioned structure of the joint apparatus makes the wearer's lower limb (leg part) forward movements smoother. The joint apparatus attaches to each of the long leg supporting members with the main block as the center, each carrier slidably mounted on the sides of the main block, and each long leg supporting member attached to the joint through a carrier. The long leg supporting members can be operated by the electric motor to rock smoothly. The carriers having a relative sliding movement on the sides of the main block are connected to the long leg supporting members. So that the left and right limbs (leg parts), supported by the long leg supporting members and assisted by the power-assisted joint apparatus are able to make smooth forward movements.

In one embodiment of the invention, a single pinion operated by an electric motor is installed between arc-shaped racks on the left and right carriers. The pinion gear and arc-shaped racks form a gear function as they mesh with each other. Thus, if the pinion gear rotates in one rotational direction, this is accompanied by one arc-shaped rack moving relatively forward a distance while the other arc-shaped rack moves relatively towards the rear. As a result, the arc-shaped racks move the left and right carriers which, in turn, move the left and right long leg supporting members. In other words, a wearer of an orthotic apparatus employing the power assisted joint apparatus can produce a movement such that when one of the lower limbs is moved forward the other lower limb is moved backwards and an alternate walking movement is made smoothly. Additionally, the central point of the arc of the arc-shaped groove approximates the imaginary hip joint rotation central point of the wearer when viewed from the side (refer to FIG. 3). Thus, the rotation central point of the rocking movement of the carriers and long leg support members approximately matches the wearer's hip joint rotation central position. As a result, the forward sensation of the lower limbs of the wearer approximates the rocking movement of the long leg supporting members worn on the lower limbs; the wearer feels no difference and is able to have a smooth lower limb forward movement.

In one aspect of the invention, based on a central signal (directions) from control routines, a forward movement or reverse movement of the electric motor can be freely made. Thus, based on the directions (signals) from control routines, by forward rotation or reverse rotation of the electric motor, the left and right legs (lower limbs) of the wearer can be moved forward. When one of the lower limbs has moved forward such that a foot part touches the ground, then, based on the signal from the control routines, the electric motor is put into reverse and the other remaining leg is moved forward. By alternating the forward and reverse movement of the electric motor, an alternating go-forward movement of the left and right legs (lower limbs) can be done. As a result, the wearer of this joint apparatus, with the power assist from the electric motor, can achieve a smooth alternating walking.

In another embodiment of the invention, the connecting structure of the carriers for connecting the joint apparatus to the long leg supporting members includes: an attachment being mountable onto the long leg supporting members, the attachment having a hook installed on a plate part at the plate side; and a base plate forming a part of the carrier and having a connecting groove for inserting the hooks of the attachment. The connecting structure further includes: a locking mechanism installed inside a space formed between the base plate and a cover of the base plate to maintain the connecting relationship between the attachment and the carrier base plate when the hook of the attachment is inserted inside the connecting groove; and an unlocking mechanism including a spring and push button for canceling the locking mechanism.

With the above connecting structure, assembly and disassembly of a long leg supporting member and a carrier can be achieved. In other words, the attachment and removal process can be done easily and become smoother.

DETAILED DESCRIPTION OF PREFERRED EMBODIMENTS

Figure 1:
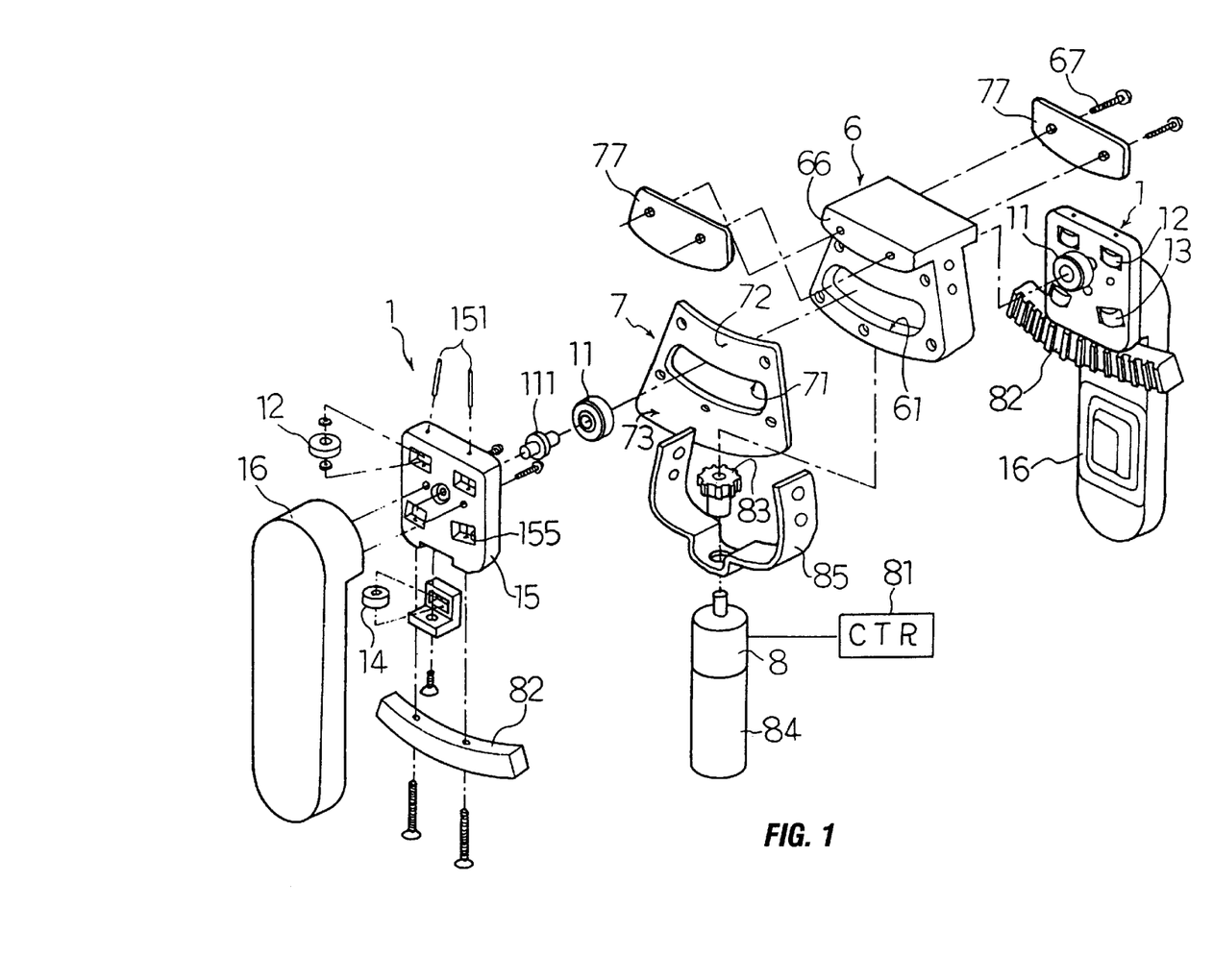
FIG. 1 is an exploded view showing the whole structure of one embodiment of a joint apparatus with power assist mechanism, using an electric motor.
Figure 4:
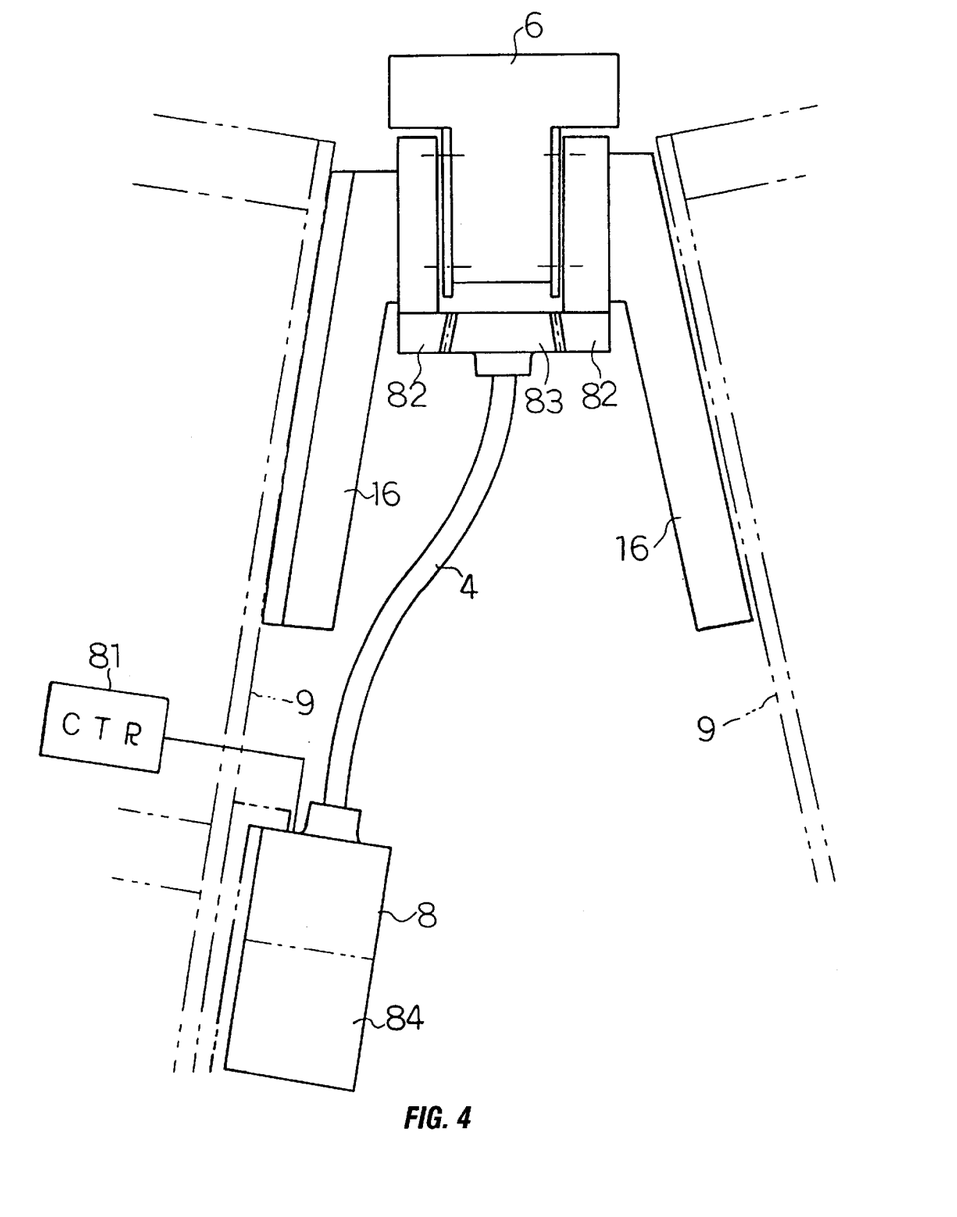
FIG. 4 shows the overall make-up of one embodiment of a joint apparatus that has power assist mechanism where an electric motor is attached to a long leg supporting member.

In one embodiment, a joint apparatus which has a power assist mechanism comprising an electric motor, as shown in FIG. 1 and FIG. 4. As shown in FIG. 1, the joint apparatus includes: a main block 6 which forms the foundation of operation for the joint apparatus and is installed between the patient's thighs; a carrier 1 installed on both sides of the main block 6 with relative slipping movement against the main block 6 and approximating the patient's (wearer's) imaginary hip rotation central point as the center for a swinging (rocking) movement, as well as, attaching to the left and right long leg support members; and an arc-shaped rack 82, installed on the bottom of the carrier 1 and forming part of an arc having its focal point approximating the imaginary hip rotating central point. The joint apparatus also includes a single pinion gear 83 which connects to the left and right arc-shaped racks 82 installed onto the left and right carriers 1; and an electric motor 8 that drives the pinion gear 83 and is able to make forward and reverse movements. Also included on the left and right carriers 1 are base plates 16, for connecting to attachments 2 which can be mounted onto the long leg supporting members 9 supporting the patient's lower limbs. In addition, the left and right long leg supporting members 9, are attached so that their opening angle is about 10 to 20 degrees, as shown in the frontal view of FIG. 2. In other words, the carriers 1 are symmetrically connected to both sides of the main block 6 and to each long leg supporting member, so that each inclination angle is about 5 to 10 degrees against the main block 6.

In this embodiment, the main block 6 is made in the form of a fan; at the base of the fan, a base part 66 with a designated width (thickness) is made. Below the base part 66, on both sides of the fan shape, is an arc-shaped groove 61 which is connected to a main roller 11 of the carrier 1. The central point ($O_1$) of the arc of the arc-shaped groove 61 is arranged so that it approximately matches the imaginary hip rotation central point of the wearer (patient), as shown in FIG. 3. The arc angle (theta) of the arc-shaped groove 61 is set in the range of about 20 to 45 degrees (refer to FIG. 2). On the top and bottom of the arc-shaped grooves 61, there is a rail formed concentrically with the arc-shaped groove 61.

Figure 2:
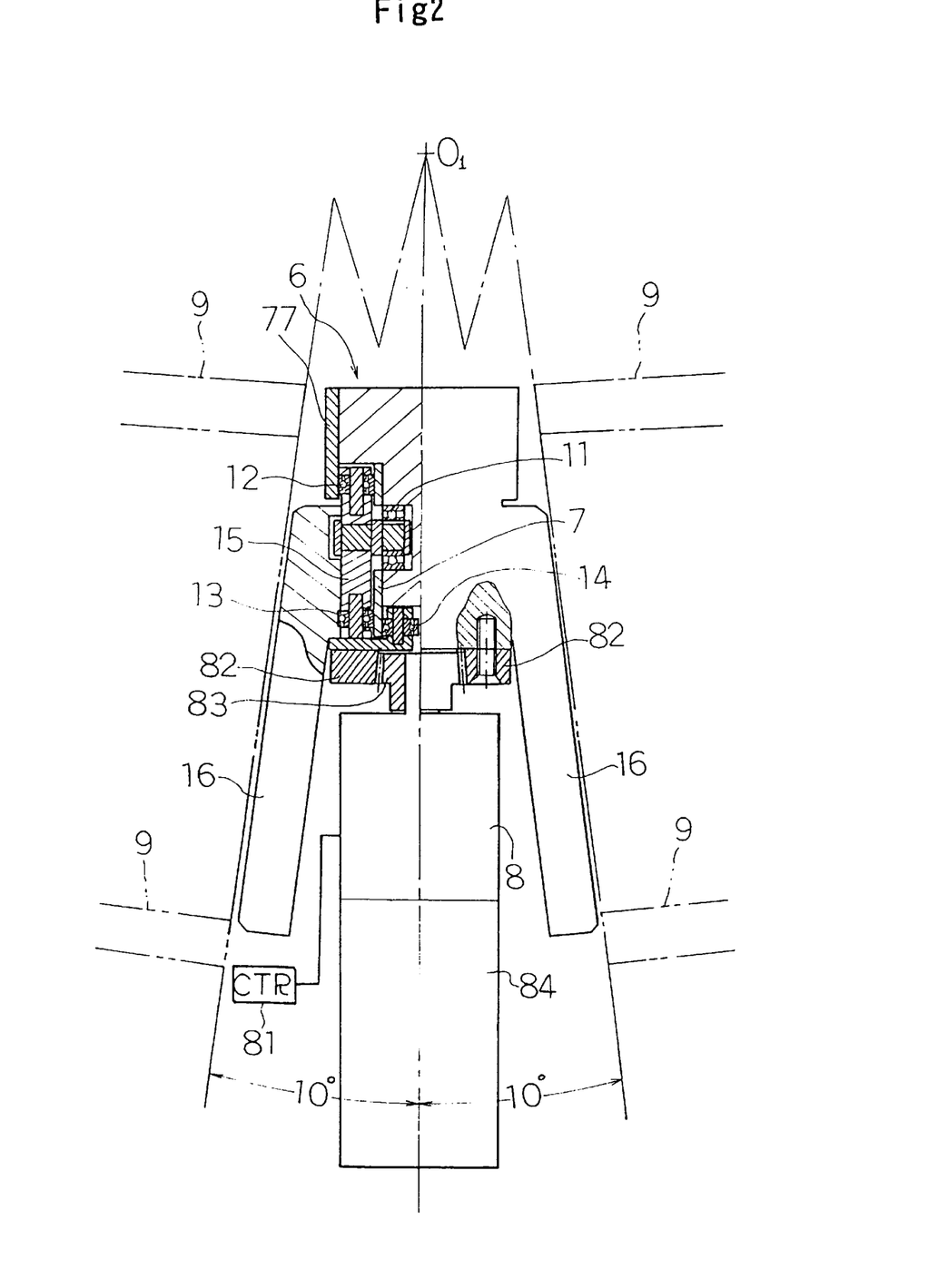
FIG. 2 is a frontal view and partial view of a broken-out figure of one embodiment of a joint apparatus with a power assist mechanism that uses an electric motor.
Figure 3:
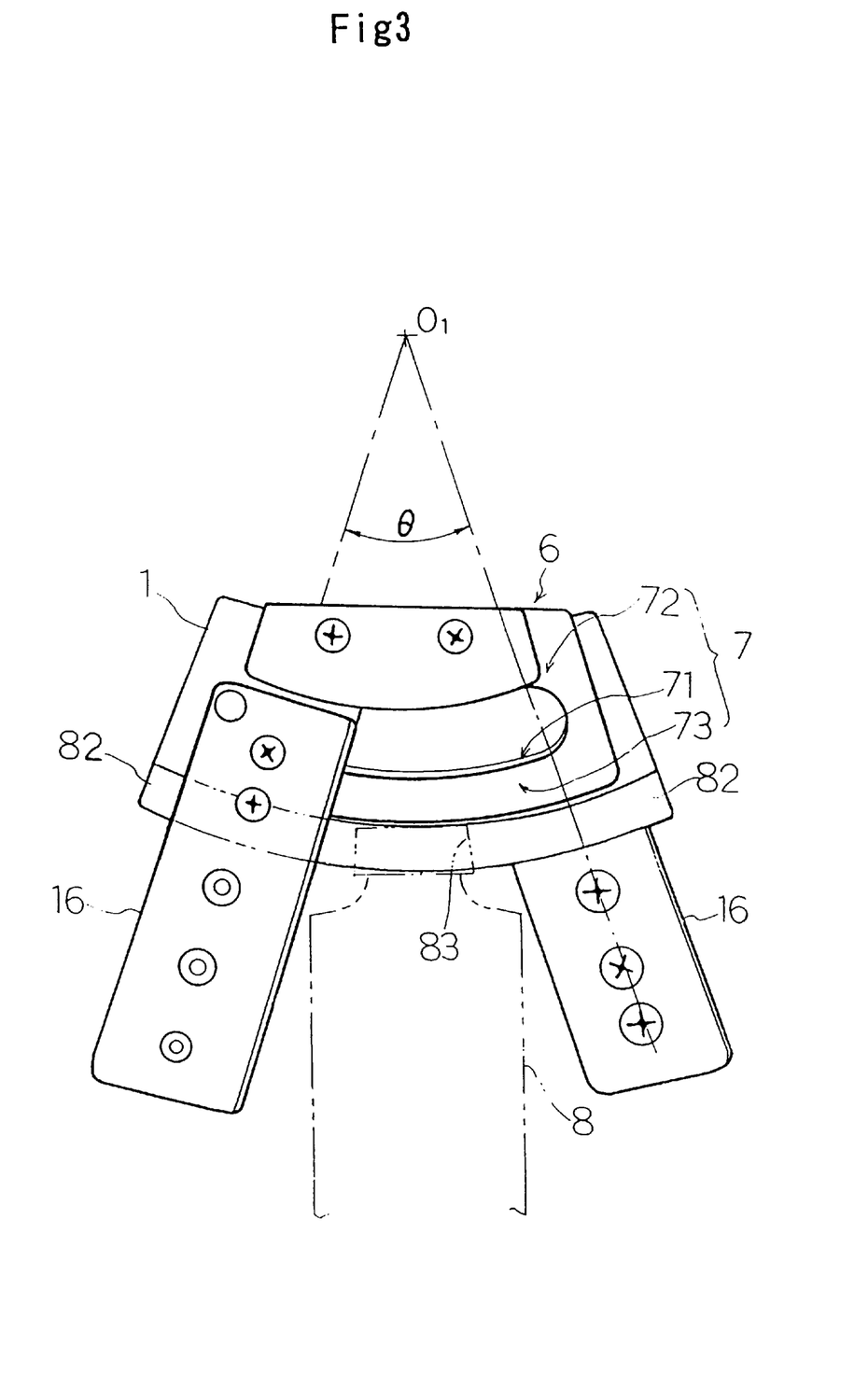
FIG. 3 is a side view of one embodiment of a joint apparatus with power assist mechanism that uses an electric motor.

In an alternative embodiment, as shown in FIG. 1 and FIG. 2, the rails 72 and 73 can be made on side plates 7. The side plates 7, made from a rigid plate, are placed on both sides of the main block 6 and have a cutout 71 aligned with the arc-shaped groove 61 on the main block 6. On the upper and lower part of each cutout there are arc-shaped rails 72 and 73 for the side rollers to rotate on. As shown in FIG. 1 and FIG. 2, side rollers 12, 13 and 14 will connect and roll on top of the rails 72 and 73. On both sides of the base 66 of the main block 6, there is a guide plate 77 that holds some of the side rollers making up the carrier 1, particularly the upper side rollers 12. The guide plates 77 can be fixed in place by designated fixtures 67, etc.

A shown in FIG. 1 and FIG. 2, the carrier 1 is connected at both sides of the main block 6 to allow relative slipping movements against the main block 6. The carrier 1 includes a carrier base 15 which has a certain thickness. At about the center of the carrier base 15, is the main roller 11 which takes on mostly the vertical load. Centered around the main roller 11 are the side rollers 12, 13, and 14, which mostly take on the heavy horizontal loads and have rotational movement at the rails 72 and 73. An arc-shaped rack 82, having inward-facing gears, is installed at the bottom part of the carrier base 15 of the carrier 1. On the arc-shaped rack 82, at the outer side of carrier 1, the base plate 16 is placed so as to overlap the arc-shaped rack 82. To the base plate 16, a long leg supporting member 9 is connected through the attachment 2, etc.

In the above structures, the main roller 11 is hung from the carrier base 15 at a central part of the carrier base 15 by a shaft 111 with a flange as shown in FIG. 1 and FIG. 2. The main roller 11 connects with the arc-shaped groove 61 to have rotating movements inside the arc-shaped groove 61. Side rollers 12, 13 and 14 are generally installed at right angles to the main roller 11 through fixing points 151, etc. The side rollers 12, 13 and 14 are installed inside windows 155 of the carrier base 15 so as to rotate freely. Side rollers 12, installed on the upper side of the main rollers 11, are placed in between the guide plate 77 and side plate 7, and rotate in between both. The other side rollers 13 and 14 are placed at the lower side at the rail 73 formed at the bottom part of the side plate 7 to rotate there (refer to FIG. 1). Each Roller 11, 12, 13 and 14 is made of plastic material or metals, etc., such as steel. With strength and rigidity considered, miniature bearings made of steel were used.

The base plate 16, installed onto the carrier base 15 of the carrier 1, is assembled as a single body with the carrier base 15 and, accordingly, has a slipping or rocking movement at both sides of the main block 6. The base plate 16 is made of metal material, etc., to have a strong strength and rigidity. The base plate 16, as a single body with a cover 17, is assembled onto the carrier base 15 of the carrier 1 by a clamping method using bolts, etc. In one embodiment of the invention, the inclination angle of the base plate is 5 to 10 degrees from the main block 6, as shown in FIG. 2. Onto the base plate 16, a long leg supporting member 9 can be connected (assembled) through the attachment 2. Thus, the left and right long leg supporting members 9, installed against the main block 6 with the above-mentioned inclination angle, have an opening angle, as viewed from the front, of about 10 to 20 degrees.

At the bottom part of the carrier base 15 of the carrier 1, an arc-shaped rack 82 is installed, as shown in FIG. 1. The arc-shaped rack 82 has a circumference pitch line which forms an arc with the central point, $O_1$, which approximates the imaginary hip rotational central point, as shown in FIG. 3. The left and right arc-shaped racks 82 are formed, as shown in FIG. 1 and FIG. 2. A pinion gear 83 connects with the left and right arc-shaped racks 82. The pinion gear 83, either directly or through decelerating mechanisms, etc., is connected to the electric motor 8. The pinion gear 83 and electric motor 8, as well as the battery 84, are attached to the bottom part of the main block 6 through a bracket 85, as shown in FIG. 1. In one embodiment of the invention, the electric motor 8 and battery 84, may be attached around the long leg supporting member 9 as shown in FIG. 4. In this case, a flexible shaft 4 is placed between this electric motor 8 and the pinion gear 83. Through this flexible shaft 4, the power from the electric motor 8 is appropriately transferred to the pinion gear 83. Also, there is a control routine 81 to control forward and reverse operation of the electric motor 8. The control routine 81 is primarily formed with a microcomputer.

The function of the joint apparatus in an embodiment having a structure as described above and presented in the figures will now be explained. Particularly, a paraplegic patient wearing the orthotic apparatus consisting of long leg supporting members 9 and the orthotic joint apparatus of this invention is able to make a smooth alternating walk using supplemental devices such as crutches. First, based on the direction (signal) from the control routine 81, the electric motor 8, able to rotate in both forward and reverse, can be directed to rotate in one rotational direction, for example, making it to go forward. The rotational movement of the electric motor 8 is conveyed to the pinion gear 83. On both sides of the pinion gear 83, there is an arc-shaped rack 82 connected to the carrier 1 and in meshing engagement with the pinion gear to form a gear mechanism. Thus, when the pinion gear 83 and the electric motor 8 move in one rotational direction, for example, forward, along with this, the left and right arc-shaped racks 82, will move in opposite directions, for twice the value of their stroke capacity. As a result, the arc-shaped racks 82 and the left and right carrier 1, working as a unit body, will move the left and right long leg supporting members 9 relatively twice a distance. In other words, the joint apparatus is able to move the left and right long leg supporting members, and the wearer of the orthotic apparatus can move forward one of his lower limbs. Simultaneously, the other lower limb will be pulled backwards, relatively speaking, such that the left and right lower limbs separate twice the distance.

By performing the above function, one of the lower limbs (legs) is pushed forward, and the other lower limb is pushed backwards. When a foot touches the ground, based on the signal from the control routine 81, the electric motor 8 is given a reverse movement. In this way, the alternate lower limb is moved forward. Thus, by alternately moving, based on the signal from the control routine 81, the forwarding or reversing of the electric motor 8 will cause the left and right legs (lower limbs) of the wearer to make an alternate forward movement. As a result, the wearer of the orthotic joint will be able to make a smooth alternating walk with the power assist of the electric motor 8.

Now considering the carrier 1, which makes up the joint apparatus that is the foundation of a forward moving motion. Each Roller 11, 12, 13 and 14 installed on the carrier 1 is able to move relatively (rotate) inside the arc-shaped grove 61 of the main block 6 or on the rails 72 and 73. The central point of the arc of the arc-shaped groove 61 and the concentrically formed rails 72 and 73 approximately matches the imaginary hip rotating central point ($O_1$) of the wearer, from a side view (refer to FIG. 3). As a result, the feeling of moving the lower limb (leg part) forward by the wearer almost matches the rocking movement of the long leg supporting member attached to the lower limb (leg part). Thus, the wearer becomes able to make a smooth lower limb forward movement without a sense of feeling the difference.

In one embodiment of the invention, the carrier 1 and the long leg supporting member connected to the carrier 1 have an inclination angle of about 5 to 10 degrees when viewed from the front, as shown in FIG. 2, in other words, a 10 to 20 degree open angle is maintained. Thus, at the side rollers 12, 13 and 14 installed in the carrier 1, there is a danger that a force of moment may occur due to the above-mentioned inclination angle. However, since the side rollers 12 are installed in between a side plate 7 guide plate made of high rigidity, are installed on both sides of the main block, as shown in FIG. 2, they can sufficiently counter the above-mentioned moment forces. As a result, the rotational movement of these side rollers 12, 13 and 14 over the rails 72 and 73 can be done smoothly, and the relative slipping or rocking movement of the carrier 1 and the long leg supporting member 9 against the main block 6 will become smooth. In other words, each left and right lower limb (leg part) supported by the long leg supporting member, with help from the power assisting electric motor 8, can make a smooth forward movement.

Figure 5:
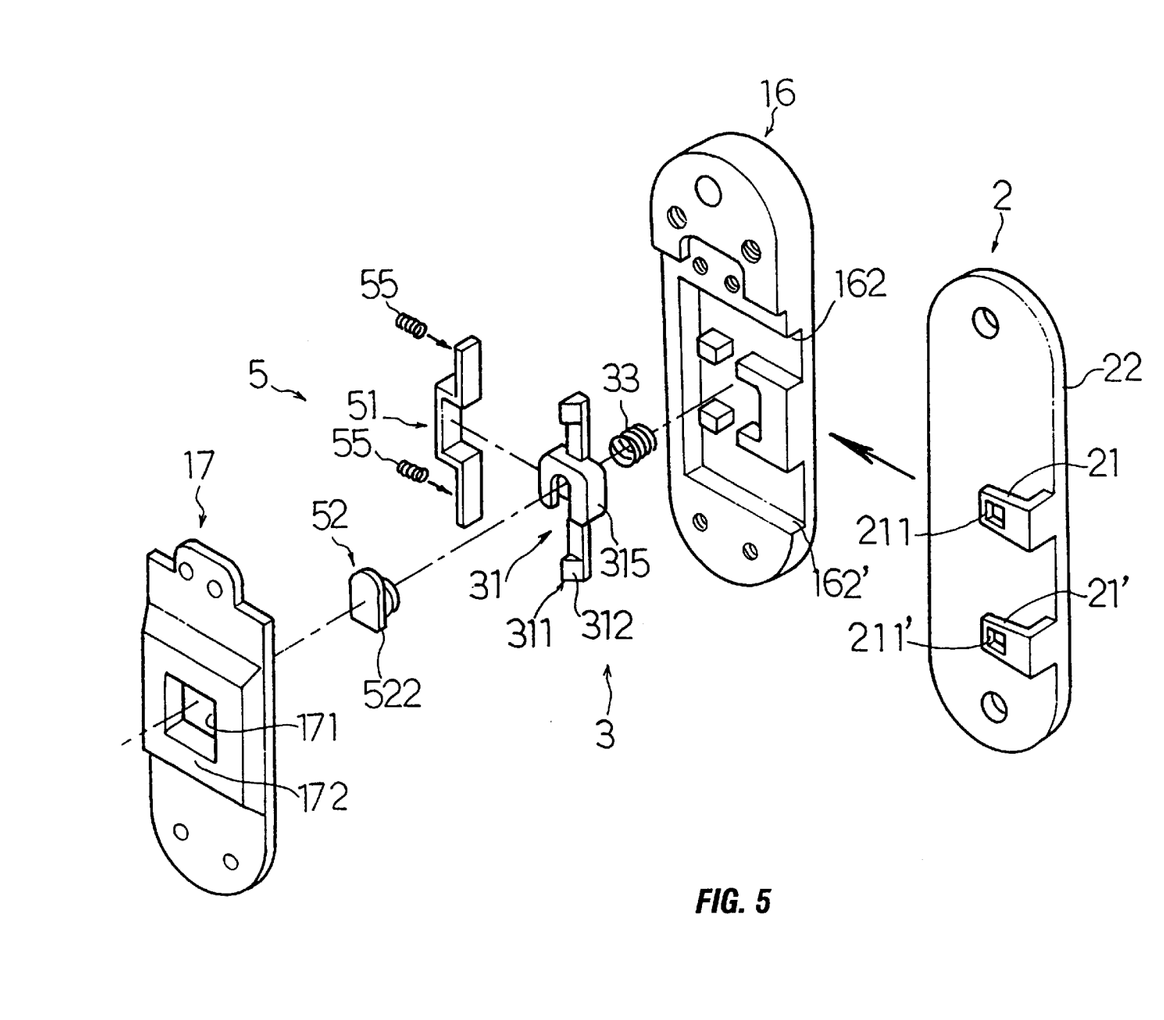
FIG. 5 is an exploded view of the overall structure of one embodiment of a carrier and attachment which connect together so that the attaching and removal is easy between the joint apparatus and the long leg supporting member.
Figure 6:
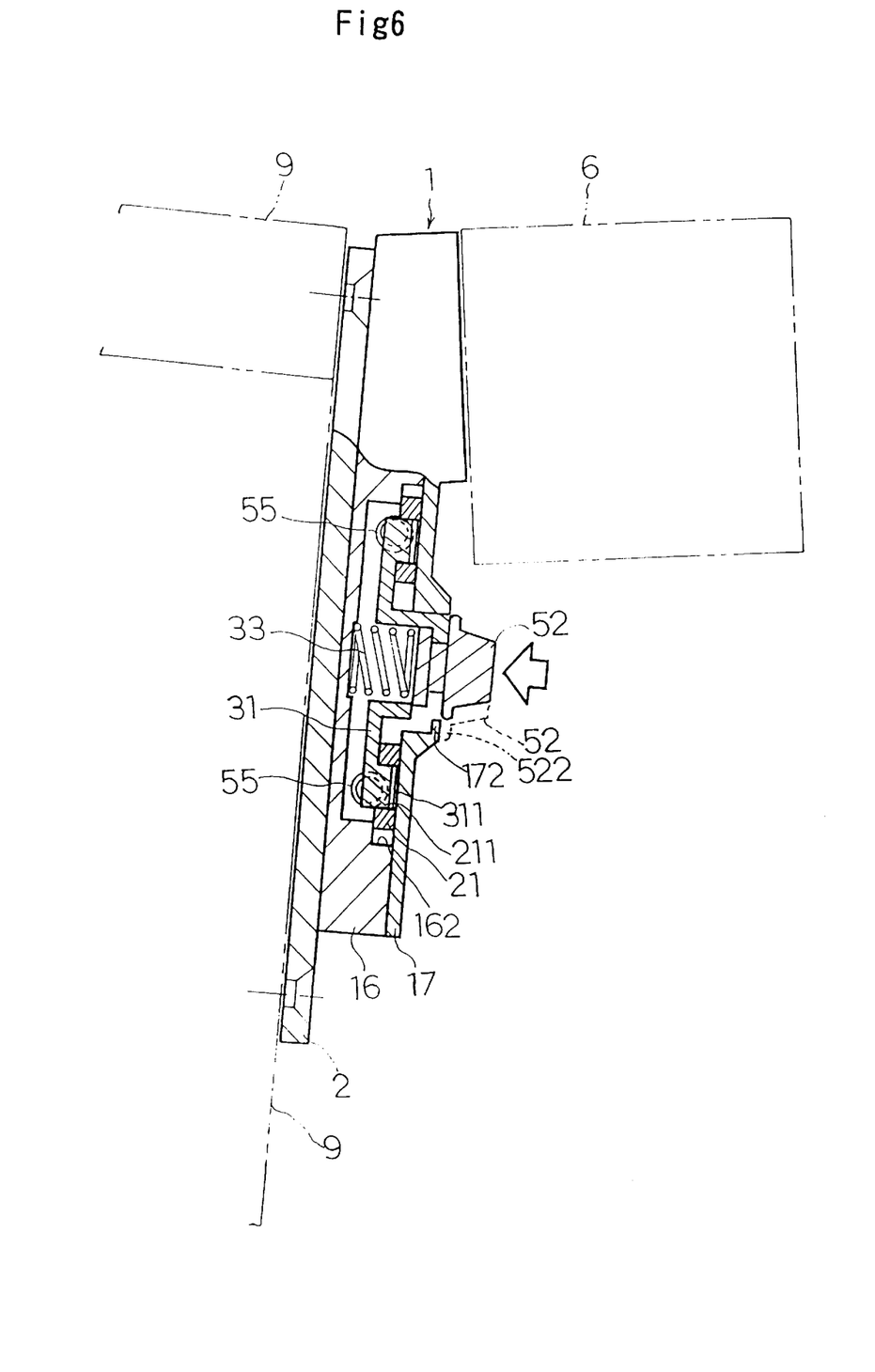
FIG. 6 is a cross section showing the condition when one embodiment of a carrier and base plate as part of a joint apparatus and an attachment mounted on of a long leg supporting member are connected to each other.
Figure 7:
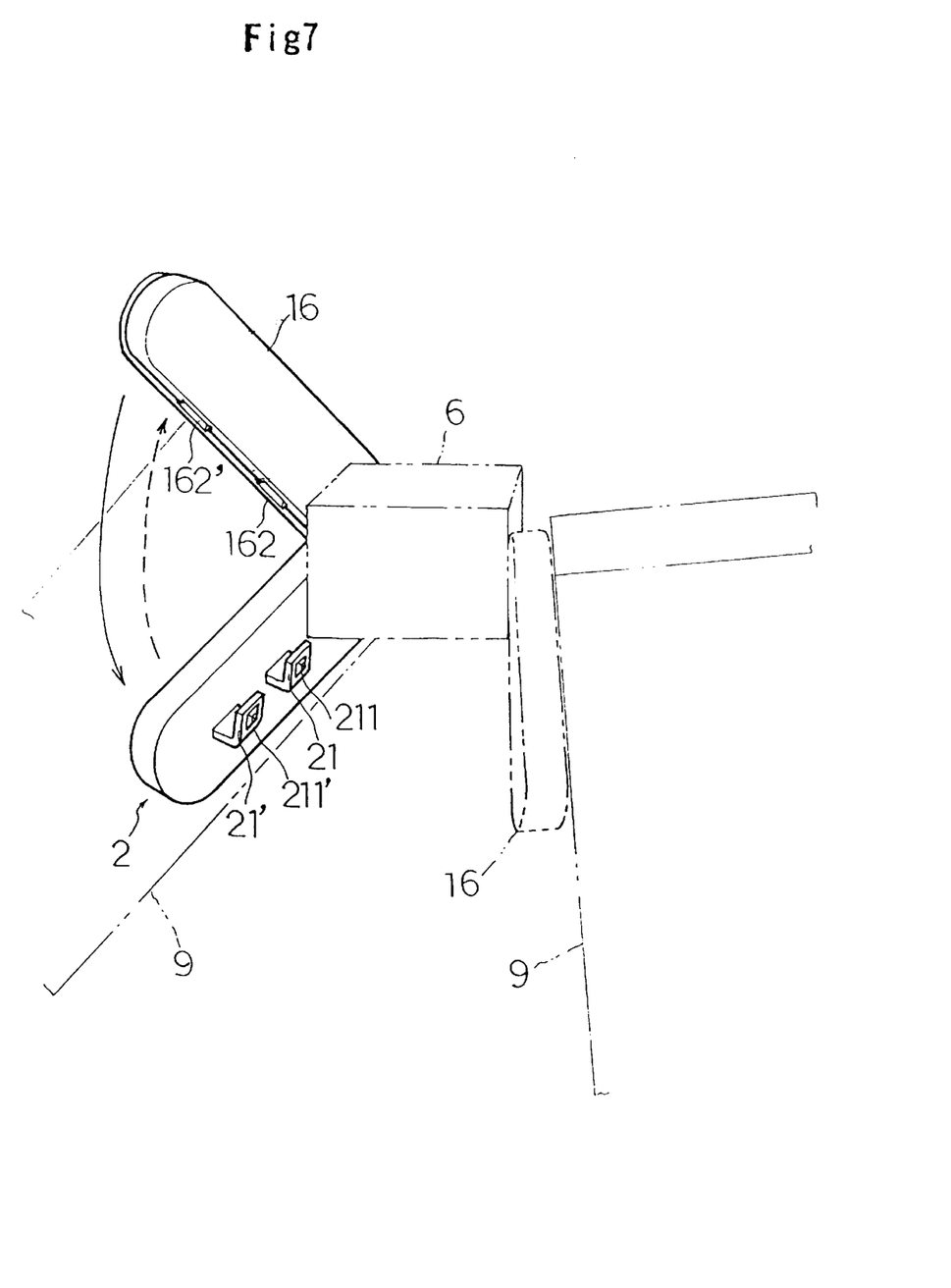
FIG. 7 shows the movement condition of a carrier and a base plate, which are parts of one embodiment of ajoint apparatus group.

In another embodiment of the invention, a connecting mechanism allows the attachment and removal of the the joint apparatus to and from a long leg supporting member attached to the patient's leg, as shown in FIG. 5 through FIG. 7. First, the connecting mechanism, as shown in FIG. 6, is made up of a carrier 1, installed in between the patient's thighs, and connected to the main block 6, which forms the foundation of the joint apparatus. The carrier 1 is connected to have a relative slipping movement against the side of the main block 6 with the center of the swinging movement (rocking) approximately the patient's (wearer) imaginary hip rotationary central point. The joint connecting mechanism includes an attachment 2 made so that attaching or removal is possible from the base plate 16 of the carrier 1, and attached to the upper end part of the long leg supporting member 9, which in turn is attached to the lower limb of the patient.

In the basic structure of the attachment 2, as shown in FIG. 6 and FIG. 7, a clamping device, such as screws, may be employed to attach the attachment 2 onto the long leg supporting member. The attachment 2, as shown in FIG. 5 and FIG. 7, includes a plate part 22, which becomes the attachment site and support foundation for the above-mentioned long leg supporting member, and two hooks 21 and 22 installed at the sides of the plate part 22 for connecting the attachment 2 to the base plate 16 of the carrier 1. At the tip of the hooks 21 and 21' are recesses 211 and 211' having a fitting hole for locking in a lock nail 311 of a locking mechanism that will be described later.

The Carrier 1, can be attached through a swinging movement and readily attach to and detach from the attachment 2, as shown in FIG. 6. The carrier basically includes: a carrier base 15 (refer to FIG. 1), with a roller, etc., formed to enable relative slipping movement and swinging movement of the above-mentioned main block 6; and a base plate 16, that is connected into a unitary body with the carrier base 15, and which is used to connect the attachment 2. The carrier also includes a cover 17, which is installed on a side of the base plate 16, to house the base plate 16 items to be described later (i.e., the locking mechanism 3, unlocking mechanism 5, etc.).

On the side of one end of the base plate 16, as shown in FIG. 5, there are connecting grooves 162 and 162' where the hooks 21 and 21' on the attachment 2 are inserted. In the inner areas, where connecting grooves 162 and 162' are installed, a designated space is made to house the later-to-be-described locking mechanism 3 and unlocking mechanism 5. The cover 17 is installed on the top side of the base plate 16 for holding such things as the connecting grooves 162 and 162' with space made to pair with the base plate 16. At the central area of the cover 17, there is a push button 52, for operating the unlocking mechanism, and an operating opening 171.

Around the operating opening 171, there is a flange 172 and the push button 52 for the unlocking mechanism 5 which is connected to the unlocking mechanism 5 for its activation (broken lines. FIG. 6).

The locking mechanism 3 and the unlocking mechanism 5, herein described, are installed near the connecting grooves 162 and 162' of the carrier 1. First, the Locking Mechanism 3 is made up of a locking part 31, which maintains the hooks 21 and 21' of the attachment 2 when inserted into the connecting grooves 162 and 162' of the base plate 16 of the carrier 1, such that both parts are connected and maintained within this part. The locking mechanism 3 also includes a spring 33, which is installed at a boss 315 made in the central area of the locking part 31. The locking mechanism 3 functions by pressing the locking part 31 which connects to hooks 21 and 21' of the carrier 1. For connecting to both ends of the bar type locking part 31, there are recesses 211 and 211' for the locking in the hooks 21 and 21' of the attachment 2 and locking nails 311 which have tapered surfaces 312 for guiding the locking nails 311 into the recesses during the insertion of the hooks 21 and 21'.

The unlocking mechanism 5 of the invention, which cancels the locked condition of the locking mechanism 3, includes a push bar 51, which is set deep inside the connecting grooves 162 and 162' of the base plate 16 and functions by pushing the hooks 21 and 21', inserted into the connecting grooves 162 and 162', to the outside of the grooves 162 and 162'. The unlocking mechanism also includes springs 55, which function to push out the hooks 21 and 21' with the push bar 51; and a push button 52, which is installed at the boss part 315 of the locking part 31 and functions to cancel the connection between the locking nail 311 of the locking part 31 and the recesses 211 and 211' on the hooks 21 and 21'. The push button 52 bottom part is connected at the boss 315 of the locking part 31, and its upper part has a flange 522. The flange 522, during the locking process, connects to the flange 172 of the cover 17 (see broken line of FIG. 6). The push button 52, basically, is inside the push button operating hole (operating hole) 171 of the cover 17, and by pressing it in the direction of the arrow, the unlocking mechanism is activated.

The functional conditions of this connecting mechanism can be described based on FIG. 7. First, in connecting the long leg supporting member and the joint apparatus, as shown in FIG. 7, when the long leg supporting member is worn at the lower limb by the patient himself, the attachment 2 is connected to the long leg supporting member such that the hooks 21 and 21' made in the attachment 2 are facing upwards. The carrier 1 and base plate 16, which are attached to the sides of the main block 6 to have a swinging movement (rocking) against the main block 6, are operated, as shown by the solid line in FIG. 7. The connecting grooves 162 and 162', formed at the sides of the base plate 16 of the carrier 1, will connect with hooks 21 and 21' made in the attachment 2. By this, the attachment 2 and base plate 16 of the carrier 1 come together. Therefore, by a swing movement of the base plate 16, the connection between the attachment 2 and the carrier 1 can be made. In other words, connection between the long leg supporting members and the joint apparatus can easily be achieved. Thus, patients using the orthotic joint apparatus and wearing the long leg supporting members, without moving his lower limbs to the left or right, become able to connect this joint apparatus to the long leg supporting member 9.

In the condition where such long leg supporting member 9 and this joint apparatus are connected, the connection of both parts can be canceled. First, the push button 52, which is in the lock position, is moved as in FIG. 6, from the dotted line to the solid line position, and the connection with the flange 172 of cover 17 is cancelled. Then, the push button 52 is pushed in the direction of the arrow, against the spring resistance of spring 33 (push). By this, the locking nail 311 part made in the lock part 31 of the locking mechanism 3, will be detached from the locking recess 211 and 211' of the hooks 21 and 21' of the attachment 2. At the same time, the springs 55 and push bar 51 of the locking mechanism 5 will operate to push the tip parts of the hooks 21 and 21' of the attachment 2 out from the connecting grooves 162 and 162' of the base plate 16 of the carrier 1. By doing this, the connecting relationship of the attachment 2 and the base plate 16 of the carrier 1 is cancelled, and the carrier 1, as shown in dotted arrow line in FIG. 7, can be lifted up. Once the connecting relation is canceled, separation of the long leg supporting member and joint apparatus can be done. This series of tasks can be done by the patient without moving the lower limb sideways (horizontally).

We claim:

1. A joint for an orthotic apparatus comprising:

a main block having arc-shaped grooves formed on opposite sides of the main block and a pair of rails separated by each arc-shaped groove;

a pair of carriers slidably mounted on the opposite sides of the main block, each carrier having a main roller in rolling engagement with one of the arc-shaped grooves and a plurality of side rollers adapted to roll on the rails;

an arc-shaped rack mounted on each carrier and arranged concentrically with the arc-shaped grooves;

a base plate connected to each carrier, the base plate being adapted to be attached to a leg supporting member;

a pinion gear mounted proximal to the main block and in meshing engagement with each arc-shaped rack; and an electric motor for driving the pinion gear.

2. The joint for an orthotic apparatus as claimed in claim 1, wherein a side plate is attached to each side of the main block, the side plate comprising an arc-shaped cutout aligned with each arc-shaped groove and rails on which the side rollers rotate.

3. The joint for an orthotic apparatus as claimed in claim 1, wherein the electric motor is directed to operate forward or in reverse based on control directions from a designated control routine.

4. A joint for an orthotic apparatus comprising:

a main block having an arc-shaped groove formed on each of opposite lateral sides of the main block;

a pair of carriers, each carrier slidably mounted on the opposite lateral sides of the main block and having a main roller in rolling engagement with the arc-shaped groove; and an attachment removably coupled to each carrier and securely connectable to a long leg supporting member to facilitate connection and removal of the carrier to the long leg supporting member.

5. The joint for an orthotic apparatus as claimed in claim 4, wherein a coupling structure for removably coupling the carrier and attachment comprises:

a base plate mounted on the carrier and having a connecting groove formed on one side of the base plate;

a plate part of the attachment being mountable onto the long leg supporting member;

a hook formed at a side of the plate part for engaging with the connecting groove of the base plate;

a locking mechanism disposed deep inside the connecting groove and arranged to lock the hook of the plate part into the connecting groove of the base plate to maintain connection between the attachment and the carrier; and an unlocking mechanism disposed proximal to the locking mechanism and arranged to unlock the hook from the connecting groove for disconnecting the attachment from the carrier.

* * * * *